United States Patent [19]

Roth et al.

[11] Patent Number: 4,808,621

[45] Date of Patent: Feb. 28, 1989

[54] TRANS-6-[2-(N-HETEROARYL-3,5-DISUB-STITUTED)PYRAZOL-4-YL)-ETHYL]- OR ETHENYL]TETRAHYDRO-4-HYDROXYPY-RAN-2-ONE INHIBITORS OF CHOLESTEROL BIOSYNTHESIS

[75] Inventors: Bruce D. Roth, Ann Arbor; Drago R. Sliskovic, Ypsilanti, both of Mich.

[73] Assignee: Warner-Lambert Company, Morris Plains, N.J.

[21] Appl. No.: 48,473

[22] Filed: May 18, 1987

Related U.S. Application Data

[63] Continuation-in-part of Ser. No. 882,327, Jul. 7, 1986, abandoned.

[51] Int. Cl.[4] .................. C07D 405/04; C07D 405/06; A61K 31/44
[52] U.S. Cl. .................................... 514/341; 546/104; 546/159; 546/279; 544/322; 544/326; 544/328; 544/330; 544/331; 548/152; 548/217; 548/483; 548/374

[58] Field of Search .................. 546/279; 514/341

[56] References Cited

U.S. PATENT DOCUMENTS 4,767,775  8/1988  Jelich et al. .................. 514/379

Primary Examiner—Alan L. Rotman
Attorney, Agent, or Firm—Ronald A. Daignault

[57] ABSTRACT

Certain trans-6-[2-(N-heteroaryl-3,5-disubstituted)-pyrazol-4-yl)ethyl]- or ethenyl]tetrahydro-4-hydroxy-2H-pyran-2-ones and the corresponding ring-opened acids derived therefrom which are potent inhibitors of the enzyme 3-hydroxy-3-methylglutarylcoenzyme A reductase (HMG CoA reductase) and are thus useful hypolipidemic or hypocholesterolemic agents. Pharmaceutical compositions containing such compounds, and a method of inhibiting the biosynthesis of cholesterol employing such pharmaceutical compositions are also disclosed.

5 Claims, No Drawings

TRANS-6-[2-(N-HETEROARYL-3,5-DISUBSTITUTED)PYRAZOL-4-YL)-ETHYL]- OR ETHENYL]TETRAHYDRO-4-HYDROXYPYRAN-2-ONE INHIBITORS OF CHOLESTEROL BIOSYNTHESIS

CROSS-REFERENCE TO RELATED APPLICATIONS

This application is a continuation-in-part of application Ser. No. 882,327 filed July 7, 1986, now abandoned.

BACKGROUND OF THE INVENTION

The present invention is related to compounds and pharmaceutical compositions useful as hypocholesterolemic and hypolipidemic agents. More particularly, this invention concerns certain trans-6-[2-(N-heteroaryl-3,5-disubstituted)pyrazol-4-yl)ethyl]- or ethenyl]tetrahydro-4-hydroxy-2H-pyran-2-ones and the corresponding ring-opened acids derived therefrom which are potent inhibitors of the enzyme 3-hydroxy-3-methylglutaryl-coenzyme A reductase (HMG CoA reductase), pharmaceutical compositions containing such compounds, and a method of inhibiting the biosynthesis of cholesterol employing such pharmaceutical compositions.

High levels of blood cholesterol and blood lipids are conditions involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine*, 305, No. 9, 515–517 (1981). It has now been established that lowering LDL-C levels affords protection from coronary heart disease (cf. *Journal of the American Medical Association*, 251, No. 3, 351–374 (1984).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer et al., *Proc. Soc. Exper. Biol. Med.*, 102: 270 (1959) and F. H. Hulcher, Arch. Biochem. Biophys., 146: 422 (1971)).

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al., *J. Chem. Soc. Perkin I* (1976) 1165.

U.S. Pat. No. 4,255,444 to Oka et al. discloses several synthetic derivatives of mevalonolactone having antilipidemic activity.

U.S. Pat. Nos. 4,198,425 and 4,262,013 to Mitsue et al. disclose aralkyl derivatives of mevalonolactone which are useful in the treatment of hyperlipidemia.

U.S. Pat. Nos. 4,375,475 to Willard et al. discloses certain substituted 4-hydroxytetrahydropyran-2-ones which, in the 4(R)-trans-stereoisomeric form, are inhibitors of cholesterol biosynthesis.

Published PCT application WO No. 86/00307 discloses certain pyrazole analogs and derivatives of mevalonolactone having utility as hypolipoproteinemic and antiatherosclerotic agents.

SUMMARY OF THE INVENTION

In accordance with the present invention, there are provided certain trans-6-[2-N-heteroaryl-3,5-substituted-pyrazol-1-yl)ethyl]- or ethenyl]tetrahydro-4-hydroxy-2H-pyran-2-ones and the corresponding ring-opened hydroxy-acids derivative therefrom which are potent inhibitors of cholesterol biosynthesis by virtue of their ability to inhibit the enzyme 3-hydroxy-3-methylglutaryl coenzyme A reductase (HMG-CoA reductase).

In particular, in its broadest aspect the present invention provides compounds of structural Formula I

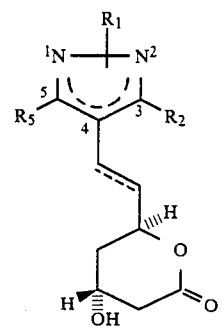

wherein $R_1$ is 2-, 4-, or 5-pyrimidinyl; 2-, 3-, or 4-pyridinyl; 2-, 3-, or 4-quinolinyl; 9-acridinyl, 3-, 4-, or 5-pyrazolyl; 2-, 4-, or 5-imidazolyl; 2-benzimidazolyl, 2-benzothiazolyl; 2-, or 3-indolyl, 2-, or 3-furanyl; or 2-, or 3-thienyl.

$R_2$ is alkyl of from one to three carbon atoms or trifluoromethyl.

$R_5$ is a saturated carbocyclic ring of from four to seven carbon atoms optionally substituted with alkyl of from one to three carbon atoms; 2-norbornyl; 2-norbornenyl; bicyclo[2.2.2]octyl;

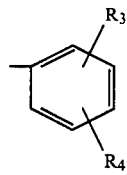

Where $R_3$ and $R_4$ are independently hydrogen, alkyl of from one to three carbon atoms, chlorine, or fluorine.

The dotted line in the bridging group connecting the substituted pyrazole group to the pyran-2-one ring is meant to indicate that the bridging group may be either an ethylene (i.e. —CH$_2$CH$_2$—) or ethenylene (i.e. —CH=CH—) group.

The dotted lines in the pyrazole nucleus in Formula I above are meant to indicate that the substituent $R_1$ may be attached to the nitrogen atom at position 1, with double bonds between the atoms at positions 2-3 and 4-5 or, alternatively, $R_1$ may be attached to the nitrogen atom at position 2 with double bonds between the atoms at positions 1-5 and 3-4. (All position numbers corresponding to those in structural Formula I above.)

Also contemplated as falling within the scope of the present invention are the hydroxy acids, and pharmaceutically acceptable salts thereof, corresponding to the opening of the lactone ring of the compounds of structural Formula I above.

In another aspect of the present invention, there is provided a method of preparing the compounds of structural Formula I above which comprises the steps of (a) first reacting a compound of structural Formula II

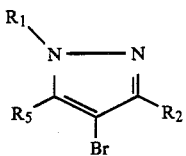

where $R_1$, $R_2$, $R_3$, and $R_4$, and $R_5$ are as defined above, with 6-ethenyl-2,2-dimethyl-1,3-dioxane-4-acetic acid, methyl or ethyl ester to form a compound of structural Formula III

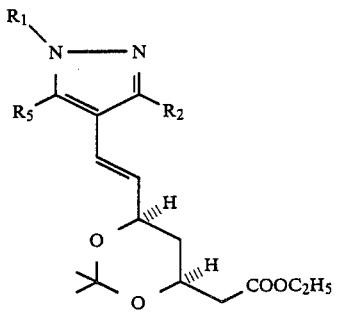

(b) hydrolyzing the product of step (a) to the corresponding acid and, if desired, cyclizing the resulting acid to form the corresponding lactone, or alternatively (c) catalytically reducing the product of step (a) by the action of hydrogen to form a compound having the structure

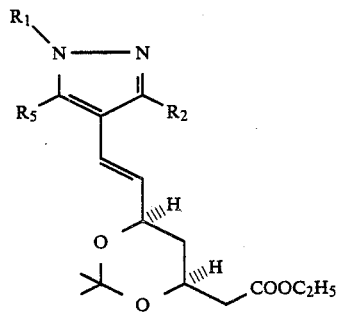

and (d) hydrolyzing the product of step (c) to the corresponding acid and, if desired, cyclizing the resulting acid to the corresponding lactone.

In yet another aspect, the present invention provides pharmaceutical compositions useful as hypolipidemic or hypocholesterolemic agents comprising a hypolipidemic or hypocholesterolemic effective amount of a compound in accordance with this invention as set forth above, in combination with a pharmaceutically acceptable carrier.

In another aspect, the present invention provides a method of inhibiting cholesterol biosynthesis in a patient in need of such treatment by administering an effective amount of a pharmaceutical composition as defined above.

DETAILED DESCRIPTION

The compounds of the present invention comprise a class of trans-6-[2-N-heteroaryl-3,5-substituted-pyrazol-1-yl)ethyl]- or ethenyl]tetrahydro-4-hydroxy-2$\underline{H}$-pyran-2-ones and the corresponding ring-opened hydroxy-acids derived therefrom in which the substituted pyrazole nucleus is attached, through an ethylene or ethenylene group to the remainder of the molecule. Preferred compounds of the present invention are those in which the bridging group between the substituted pyrazole ring and the remainder of the molecule is ethylene, i.e. —$CH_2CH_2$—.

In the compounds of the present invention, position 3 of the pyrazole nucleus (as numbered in structural Formula I above) is substituted with alkyl of from one to three carbon atoms, or trifluoromethyl. Preferred substituents at this position are lower alkyl, with 1-methylethyl being most preferred.

Position 5 of the pyrazole nucleus (as numbered in structural Formula I above) is substituted with phenyl which is monosubstituted with alkyl of from one to three carbon atoms, fluorine, chlorine or trifluoromethyl, or phenyl which is disubstituted with two groups independently selected from alkyl of from one to three carbon atoms, fluorine, chlorine, or trifluoromethyl. Preferred compounds of the present invention are those in which position 5 is substituted with 4-fluorophenyl.

The compounds of structural Formula I above possess two asymmetric carbon centers, one at the 4-hydroxy position of the pyran-2-one ring, and the other at the 6-position of the pyran-2-one ring where the alkylpyrazole group is attached. This asymmetry gives rise to four possible isomers, two of which are the R-cis- and S-cis- isomers and the other two of which are the R-trans- and S-trans- isomers. This invention contemplates only the trans- form of the compounds of Formula I above.

Examples of compounds contemplated as falling within the scope of the present invention include, but are not limited to the following:

trans-($\pm$)-6-[2-[5-(4-Fluorophenyl)-3-(1-methylethyl)-1-(2-pyridinyl)-1$\underline{H}$-pyrazol-4-yl]ethyl]tetrahydro-4-hydroxy-2$\underline{H}$-pyran-2-one.

trans-($\pm$)-6-[2-[5-(4-Fluorophenyl)-3-(1-methylethyl)-1-(2-pyridinyl)-1$\underline{H}$-pyrazol-4-yl]ethenyl]tetrahydro-4-hydroxy-2$\underline{H}$-pyran-2-one.

trans-($\pm$)-6-[2-[5-(4-Fluorophenyl)-3-(1-methylethyl)-1-(2-quinolinyl)-1$\underline{H}$-pyrazol-4-yl]ethyl]tetrahydro-4-hydroxy-2$\underline{H}$-pyran-2-one.

trans-($\pm$)-6-[2-[5-(4-Fluorophenyl)-3-(1-methylethyl)-1-(2-quinolinyl)-1$\underline{H}$-pyrazol-4-yl]ethenyl]tetrahydro-4-hydroxy-2$\underline{H}$-pyran-2-one.

trans-($\pm$)-6-[2-[5-(4-Fluorophenyl)-3-(1-methylethyl)-1-1,3'-bi-1$\underline{H}$-pyrazol-4-yl]ethyl]tetrahydro-4-hydroxy-2$\underline{H}$-pyran-2-one.

trans-($\pm$)-6-[2-[5-(4-Fluorophenyl)-3-(1-methylethyl)-1-1,3'-bi-1$\underline{H}$-pyrazol-4-yl]ethenyl]tetrahydro-4-hydroxy-2$\underline{H}$-pyran-2-one.

trans-($\pm$)-6-[2-[5-(4-Fluorophenyl)-1-(1$\underline{H}$-imidazol-4-yl)-3-(1-methylethyl)-1$\underline{H}$-pyrazol-4-yl]ethyl]tetrahydro-4-hydroxy-2$\underline{H}$-pyran-2-one.

trans-($\pm$)-6-[2-[5-(4-Fluorophenyl)-1-(1$\underline{H}$-imidazol-4-yl)-3-(1-methylethyl)-1$\underline{H}$-pyrazol-4-yl]ethenyl]tetrahydro-4-hydroxy-2$\underline{H}$-pyran-2-one.

trans-($\pm$)-6-[2-[1-(1$\underline{H}$-Benzimidazol-2-yl)-5-(4-fluorophenyl)-3-(1-methylethyl)-1$\underline{H}$-pyrazol-4-yl]ethyl]tetrahydro-4-hydroxy-2$\underline{H}$-pyran-2-one.

trans-(±)-6-[2-[1-(1H-Benzimidazol-2-yl)-5-(4-fluorophenyl)-3-(1-methylethyl)-1H-pyrazol-4-yl]ethenyl]-tetra-hydro-4-hydroxy-2H-pyran-2-one.

trans-(±)-6-[2-[1-(9-Acridinyl)-5-(4-fluorophenyl)-3-(1-methylethyl)-1H-pyrazol-4-yl]ethyl]tetrahydro-4-hydroxy-2H-pyran-2-one.

trans-(±)-6-[2-[1-(9-Acridinyl)-5-(4-fluorophenyl)-3-(1-methylethyl)-1H-pyrazol-4-yl]ethenyl]tetrahydro-4-hydroxy-2H-pyran-2-one.

trans-(±)-6-[2-[1-(2-Benzothiazolyl)-5-(4-fluorophenyl)-3-(1-methylethyl)-1H-pyrazol-4-yl]ethyl]tetrahydro-4-hydroxy-2H-pyran-2-one.

trans-(±)-6-[2-[1-(2-Benzothiazolyl)-5-(4-fluorophenyl)-3-(1-methylethyl)-1H-pyrazol-4-yl]ethenyl]tetrahydro-4-hydroxy-2H-pyran-2-one.

trans-(±)-6-[2-[5-(4-Fluorophenyl)-3-(1-methylethyl)-1-(2-thienyl)-1H-pyrazol-4-yl]ethyl]tetrahydro-4-hydroxy-2H-pyran-2-one.

trans-(±)-6-[2-[5-(4-Fluorophenyl)-3-(1-methylethyl)-1-(2-thienyl)-1H-pyrazol-4-yl]ethenyl]tetrahydro-4-hydroxy-2H-pyran-2-one.

trans-(±)-6-[2-[5-(4-Fluorophenyl)-1-(2-furanyl)-3-(1-methylethyl)-1H-pyrazol-4-yl]ethyl]tetrahydro-4-hydroxy-2H-pyran-2-one.

trans-(±)-6-[2-[5-(4-Fluorophenyl)-1-(2-furanyl)-3-(1-methylethyl)-1H-pyrazol-4-yl]ethenyl]tetrahydro-4-hydroxy-2H-pyran-2-one.

trans-(±)-6-[2-[5-(4-Fluorophenyl)-3-(1-methylethyl)-1-(1H-pyrrol-2-yl)-1H-pyrazol-4-yl]ethyl]tetrahydro-4-hydroxy-2H-pyran-2-one.

trans-(±)-6-[2-[5-(4-Fluorophenyl)-3-(1-methylethyl)-1-(1H-pyrrol-2-yl)-1H-pyrazol-4-yl]ethenyl]tetrahydro-4-hydroxy-2H-pyran-2-one.

The reaction sequence which is used to prepare compounds of the present invention is depicted schematically in the following Reaction Sequence.

The known or commercially available heteroaryl hydrazine, IV, is reacted with with the desired 1,3-disubstituted diketone, V, to produce the cyclized N-heteroaryl-substituted pyrazole, VIa or VIb. This addition may occur in either of two ways, leading to a substituted pyrazole addition product in which the heterocyclic ring substituent resides on either of the two nitrogen atoms of the pyrazole ring. The predominant product of this reaction, however, is the regioisomer in which the heterocyclic ring is attached to the nitrogen atom adjacent to the carbon which bears the substituted phenyl group (i.e., VIa).

REACTION SEQUENCE

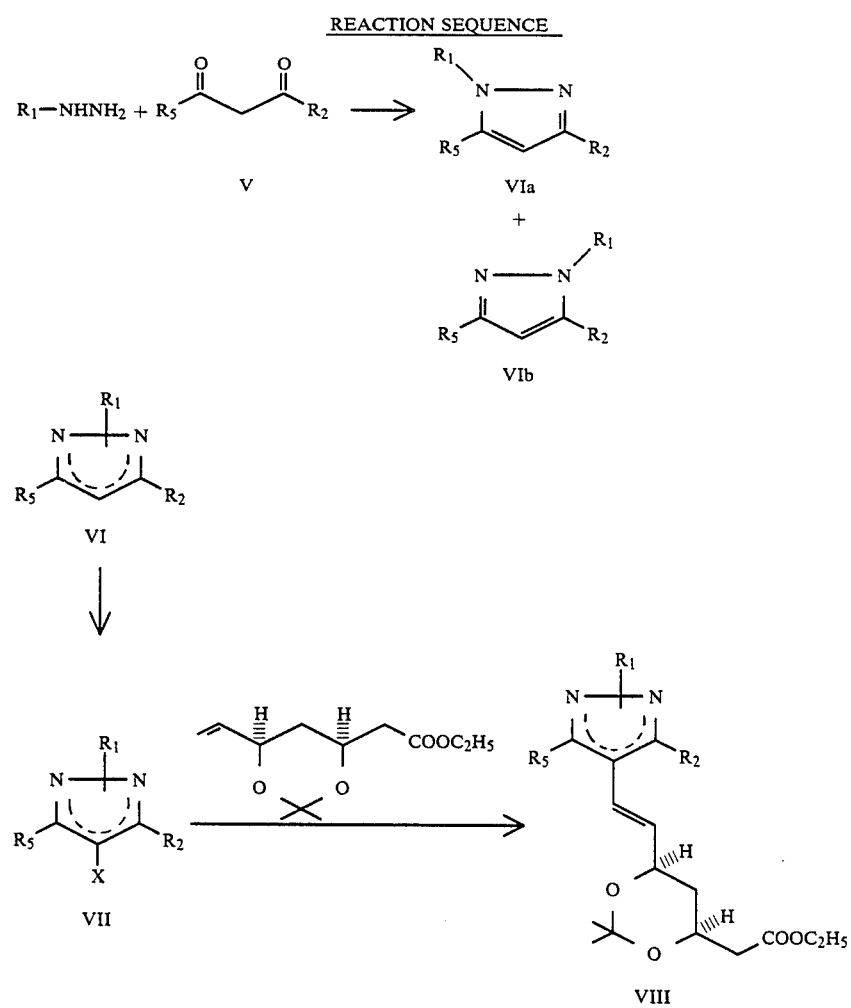

-continued
REACTION SEQUENCE

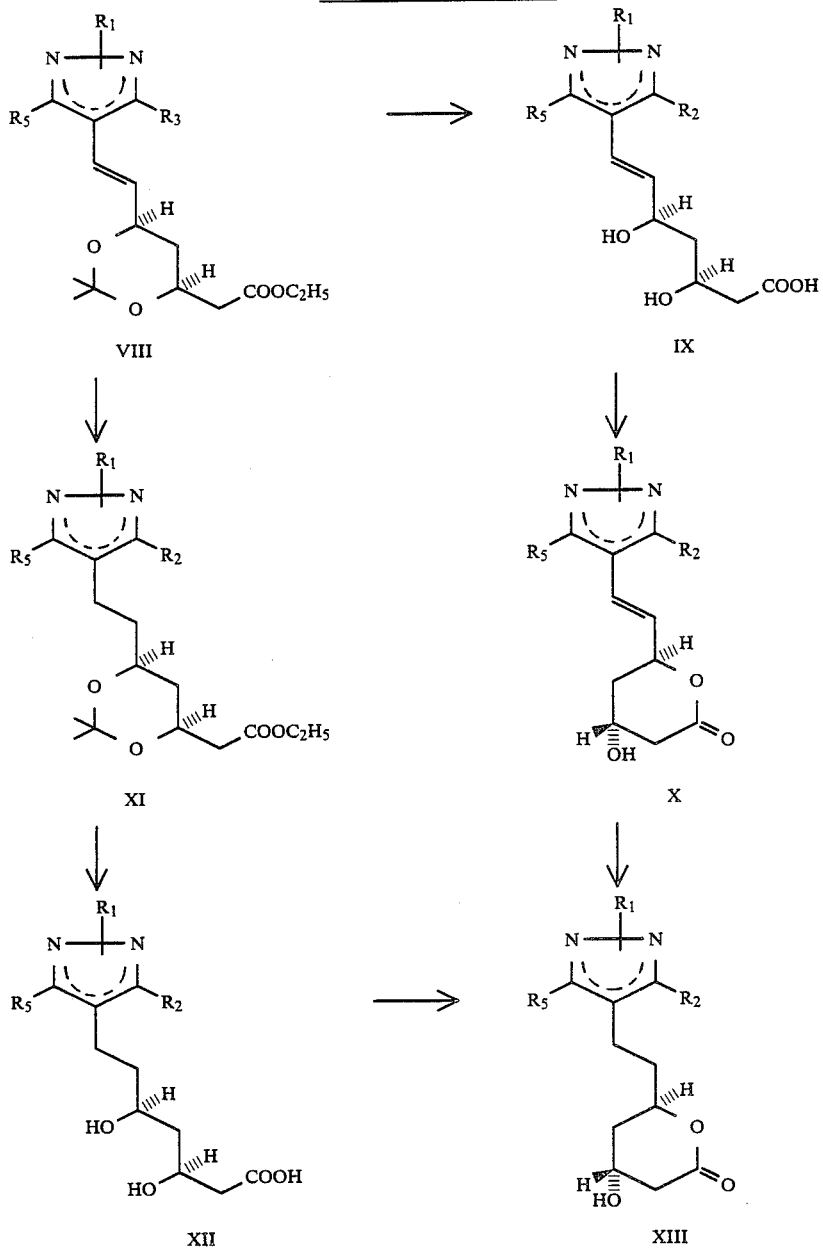

The substituted pyrazole VI is next halogenated by the action of N-bromo- or N-iodosuccinimide in a polar solvent such as dimethylformamide, typically at a temperature below about 10° C. to produce the halogenated derivatives, VII, where X is iodine or bromine.

The 4-halopyrazole compounds, VII, are coupled with 6-ethenyl-2,2-dimethyl-1,3-dioxane-4-acetic acid, methyl or ethyl ester, employing the Heck Reaction (cf. R. F. Heck, *Organic Reactions,* 27: 345–390 (1982) to form VIII.

The pyrazolyl(ethenyl)-1,3-dioxanes, VIII, are saponified and the protecting group removed in the usual manner to produce the corresponding dihydroxyacids, IX, which are employed per se, or as a pharmaceutically acceptable salt, in the pharmaceutical method of this invention. Alternatively, the acids, IX, may be cyclized to the corresponding lactones, X, under mild conditions by a dehydrating agent such as dicyclohexylcarbodiimide.

In a further alternative, the unsaturated dioxanes, VIII, are catalytically reduced under hydrogen to produce the corresponding saturated compounds, XI, which are saponified and deprotected in the usual manner to produce the saturated dihydroxyacids, XII. As with the unsaturated dihydroxyacids, the saturated dihydroxyacids, XII, are employed per se, or as a pharmaceutically acceptable salt in the pharmaceutical method of this invention, or are cyclized to the corresponding saturated lactones, XIII, generally by heating under reflux in toluene with concomitant azeotropic removal of water.

The ring-opened hydroxy acids of structural formulae IX and XII abov are intermediates in the synthesis of the lactone compounds of Formula I and may be used in their free acid form or in the form of a pharmaceutically acceptable metal or amine salt in the pharmaceutical method of the present invention. These acids react to form pharmaceutically acceptable metal and amine salts. The term "pharmaceutically acceptable metal salt" contemplates salts formed with the sodium, potassium, calcium, magnesium, aluminum, iron, and zinc ions. The term "pharmaceutically acceptable amine salt" contemplates salts with ammonia and organic nitrogenous bases strong enough to form salts with carboxylic acids. Bases useful for the formation of pharmaceutically acceptable nontoxic base addition salts of compounds of the present invention form a class whose limits are readily understood by those skilled in the art.

The free acid form of compounds of the present invention may be regenerated from the salt form, if desired, by contacting the salt with a dilute aqueous solution of an acid such as hydrochloric acid.

The base addition salts may differ from the free acid forms of the compounds of this invention in such physical characteristics as solubility and melting point, but are otherwise considered equivalent to the free acid form for the purposes of this invention.

The compounds of the present invention may exist in solvated or unsolvated form. In general, the solvated forms with pharmaceutically acceptable solvents such as water, ethanol and the like, are equivalent to the unsolvated forms for the purposes of this invention.

The compounds of this invention are useful as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

A second method (designated COR screen) employed the procedure detailed by T. Kita, et al., *J. Clin. Invest.*, (1980), 66: 1094–1100. In this method, the amount of $^{14}$C-HMG-CoA converted to $^{14}$C-mevalonate in the presence of a purified enzyme preparation of HMG-CoA reductase was measured. The micromolar concentration of compound required for 50% inhibition of cholesterol synthesis was measured and recorded as an $IC_{50}$ value.

The activity of representative examples of compounds in accordance with the present invention appears in Table 1, and are compared with that of the prior art compound, compactin.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

TABLE 1

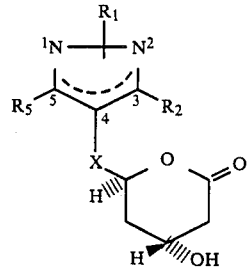

| Compound | X | $R_1$ | $R_2$ | $R_3$ | $R_4$ | $IC_{50}$ (Micromoles/liter) CSI | COR |
|---|---|---|---|---|---|---|---|
| 1 | —CH$_2$CH$_2$— | 1-(2-pyridinyl) | —CH(CH$_3$)$_2$ | H | 4-F | 0.039 | 0.11 |
| Compactin (Prior art) | | | | | | 0.026 | 0.028 |

The ability of compounds of the present invention to inhibit the biosynthesis of cholesterol was measured by two methods. A first method (designated CSI screen) utilized the procedure described by R. E. Dugan et al., *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of $^{14}$C-acetate into nonsaponifiable lipid by the rat liver homogenate is measured. The micromolar concentration of compound required for 50% inhibition of sterol synthesis over a one-hour period is measured, and expressed as an $IC_{50}$ value.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid form preparations include solutions suitable for oral or parenteral administration, or suspensions and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as hypolipidemic or hypocholesterolemic agents, the compounds utilized in the pharmaceutical method of this invention are administered to the patient at dosage levels of from 40 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of trans-6-[2-[5-(4-fluorophenyl)-3-(1-methylethyl)-1-(2-pyridinyl)-1H-pyrazol-4-yl]ethyl]tetrahydro-4-hydroxy-2H-pyran-2-one Step A—Preparation of 1-(4-fluorophenyl)-4-methyl-1,3-pentanedione A mixture of 4-fluoroacetophenone (150 g, 1.09 mol) and ethyl isobutyrate (126 g, 1.09 mol) in 1.5 liters of dioxane was added dropwise under a nitrogen atmosphere to a vigorously stirred suspension of hexane-washed sodium hydride (133 g, 3.25 mol, 58.8% NaH) in 3.0 liters of dioxane. Vigorous evolution of gas ensued, after which the mixture was heated to 80°–90° C. for four hours.

The mixture was then allowed to cool to room temperature after which it was poured into six liters of 2M hydrochloric acid. The resulting mixture was cooled to 0° C. with vigorous stirring and extracted four times with 1-liter portions of chloroform.

The combined chloroform extracts were washed twice with 500-ml portions of water, twice with 500-ml portions of brine solution, and then dried over anhydrous magnesium sulfate. The mixture was filtered to remove undissolved solids, and the filtrate was concentrated under vacuum.

Distillation of the residue yielded 116 g (50%) of 1-(4-fluorophenyl)-4-methyl-1,3-pentanedione, b.p. 100°–110° C. at 1 torr. The infrared spectrum of a thin film of the product showed principal absorption peaks at 2973 and 1603 reciprocal centimeters.

The 100 MHz proton magnetic resonance spectrum of the product in deuterochloroform showed peaks at 1.25 (doublet, J=7 Hz, 6 protons), 2.60 (multiplet, J=7 Hz, 1 proton), 6.1 (multiplet, 2 protons), 6.1 (singlet, 1 proton), 7.15 (multiplet, 2 protons), and 7.9 (multiplet, 2 protons) parts per million downfield from the tetramethylsilane signal.

Step B—Preparation of 2-[5-(4-fluorophenyl)-3-(1-methylethyl)-1H-pyrazol-1-yl]pyridine To a solution of 10 g (48 mmol) of 1-(4-fluorophenyl)-4-methyl-1,3-pentanedione in 100 ml of glacial acetic acid was added, under a nitrogen atmosphere at room temperature, 5.77 g (53 mmol) of 2-hydrazinopyridine.

This mixture was then heated at 60° C. for three hours, cooled to room temperature, and poured into 100 ml of water. The resulting mixture was extracted with diethyl ether and the organic layer was separated, washed successively with saturated sodium bicarbonate solution, water, and brine. The ether solution was dried over anhydrous magnesium sulfate, and concentrated under vacuum.

The crude product was flash chromatographed on a silica gel column, eluting with 20% ethyl acetate in hexane to yield 8.7 g of 2-[5-(4-fluorophenyl)-3-(1-methylethyl)-1H-pyrazol-1-yl]pyridine, mp 80°–81° C.

The 200 MHz proton magnetic resonance spectrum of a deuterochloroform solution of the product exhibited peaks at 8.35 (doublet, 1H); 7.0–7.8 (multiplet, 7H); 6.35 (singlet, 1H); 3.15 (multiplet, 1H); and 1.3 (doublet, 6H) parts per million downfield from the tetramethylsilane signal.

Step C—Preparation of 2-[4-bromo-5-(4-fluorophenyl-3-(1-methylethyl)-1H-pyrazol-1-yl]pyridine N-Bromosuccinimide (7.9 g, 28 mmol) was added to a mixture of 2-[5-(4-fluorophenyl)-3-(1-methylethyl)-1H-pyrazol-1-yl]pyridine (7.89 g, 28 mmol) and 30 ml of dimethylformamide at 0° C.

The resulting mixture was stirred at 0° C. for four hours and then poured into 100 ml of water. The white solid which precipitated was collected by filtration and dried to yield 9.0 g of 2-[4-bromo-5-(4-fluoro-phenyl)-3-(1-methylethyl)-1H-pyrazol-1-yl]pyridine, mp 98°–100° C.

The 200 MHz proton magnetic resonance spectrum of a deuterochloroform solution of the product exhibited peaks at 8.3 (doublet, 1H); 7.0–7.8 (multiplet, 7H); 3.1–3.2 (multiplet, 1H); and 1.4 (doublet, 6H) parts per million downfield from the tetramethylsilane signal.

Step D—Preparation of cis-(±)-ethyl 6-[2-[5-(4-fluorophenyl)-3-(1-methylethyl)-1-(2-pyridinyl)-1H-pyrazol-4-yl]ethenyl]-2,2-dimethyl-1,3-dioxane-4-acetate bis-(Tri-O-tolylphosphine)palladium chloride (0.21 g, 2 mmol%) was added to a stirred solution of 6-ethenyl-2,2-dimethyl-1,3-dioxane-4-acetic acid, ethyl ester (5.54 g, 24.3 mmol) in 30 ml of a 50:50 mixture of triethylamine and dimethylformamide.

The mixture was heated to reflux (~120° C.) and 5 g (13.9 mmol) of 2-[4-bromo-5-(4-fluorophenyl)-3-(1-methylethyl)-1H-pyrazol-1-yl]pyridine was added. This mixture was heated under reflux for two hours, at which point a further 0.15 g (1.5 mmol%) of catalyst was added. The mixture was heated under reflux for another twenty-four hours during which an additional 2 mmol% of catalyst was added to the mixture.

The mixture was then cooled to room temperature and poured into 50 ml of water. The mixture which resulted was extracted with diethyl ether, and the ether extract washed successively with portions of water and brine and then dried over anhydrous magnesium sulfate.

The ether solution was concentrated, and the crude product was flash chromatographed on a silica gel column eluting with 20% ethyl acetate in hexane to yield 1.44 g of cis-(±)-ethyl 6-[2-[5-(4-fluorophenyl)-3-(1-methylethyl)-1-(2-pyridinyl)-1H-pyrazol-4-yl]ethenyl]-2,2-dimethyl-1,3-dioxane-4-acetate.

The 200 MHz proton magnetic resonance spectrum of a deuterochloroform solution of the product exhibited peaks at 8.2 (doublet, 1H); 6.9–7.7 (multiplet, 7H); 6.3 (doublet, 1H); 5.6 (doublet of doublets, 1H); 4.3 (multiplet, 2H); 4.0 (quartet, 2H); 3.2 (septet, 1H); 2.56 (doublet of doublets, 1H); 2.4 (doublet of doublets, 1H); and 1.3–1.6 (multiplet, 17H) parts per million downfield from the tetramethylsilane signal.

Step E—Preparation of (R*,R*)-7-[5-(4-fluorophenyl)-3-(1-methylethyl)-1-(2-pyridinyl)-1H-pyrazol-4-yl]-3,5-dihydroxy-6-heptanoic acid A solution of 1.44 g (2.84 mmol) of cis-(±)-ethyl 6-[2-[5-(4-fluorophenyl)-3-(1-methylethyl)-1-(2-pyridinyl)-1H-pyrazol-4-yl]ethenyl]-2,2-dimethyl-1,3-dioxane-4-acetate in 15 ml of ethyl acetate was catalytically reduced under one atmosphere of hydrogen gas in the presence of 20% Pd/C at 25° C. for four days.

The catalyst was removed by filtration and the filtrate was concentrated. The residue was dissolved in 4 ml of 50:50 tetrahydrofuran:1 molar hydrochloric acid and stirred for three hours. The mixture was then made basic by the addition of 25% aqueous sodium hydroxide solution, and the mixture was stirred for thirty minutes.

This mixture was diluted with water, extracted with diethyl ether, and then acidified. The acidified water layer was extracted twice with ethyl acetate and the combined extracts were washed with brine and dried over anhydrous magnesium sulfate. Evaporation of the solvent yielded (R*,R*)-7-[5-(4-fluorophenyl)-3-(1-methylethyl)-1-(2-pyridinyl)-1H-pyrazol-4-yl]-3,5-dihydroxy-6-heptanoic acid.

Step F—Preparation of trans-6-[2-[5-(4-fluorophenyl)-3-(1-methylethyl)-1-(2-pyridinyl)-1H-pyrazol-4-yl]ethyl]-tetrahydro-4-hydroxy-2H-pyran-2-one The crude (R*,R*)-7-[5-(4-fluorophenyl)-3-(1-methylethyl)-1-(2-pyridinyl)-1H-pyrazol-4-yl]-3,5-dihydroxy-6-heptanoic acid from the previous step was lactonized by heating it under reflux in toluene for one hour with azeotropic removal of water. After cooling to room temperature the mixture was concentrated and the residue was flash chromatographed on a silica gel column, eluting with 75% ethyl acetate in hexane to yield pure trans-6-[2-[5-(4-fluorophenyl)-3-(1-methylethyl)-1-(2-pyridinyl)-1H-pyrazol-4-yl]-ethyl]-tetrahydro-4-hydroxy-2H-pyran-2-one, mp 182°–184° C. (after recrystallization from 10% ethyl acetate in hexane).

Analyzed for $C_{24}H_{26}FN_3O_2$ Calculated: C, 68.07%; H, 6.19%; N, 9.92%; Found: C, 67.76%; H, 6.18%; N, 9.57%.

The infrared spectrum of a potassium bromide pellet of the product exhibited principal absorption peaks at 2965, 2871, 1719, 1591, 1511, 1478, 1228, 1145, and 1051 reciprocal centimeters.

The 200 MHz proton magnetic resonance spectrum of a deuterochloroform solution of the product exhibited peaks at 8.82 (doublet, 1H); 7.0–7.9 (multiplet, 7H); 5.2 (doublet, 1H); 4.5 (multiplet, 1H); 4.1 (multiplet, 1H); 3.1 (heptet, 1H); 2.3–2.7 (multiplet, 4H); 1.6–1.8 (multiplet, 4H); and 1.3 (doublet, 6H); parts per million downfield from the tetramethylsilane signal.

Preparation of Starting Materials

Preparation of 5-hydroxy-3-oxo-6-heptenoic acid, ethyl ester

Propenal (0.1 mol, as a 2M solution in tetrahydrofuran) was added dropwise over a period of thirty minutes to a stirred solution of 0.11 mol of the lithio-sodio salt of ethyl acetoacetate in 200 ml of tetrahydrofuran which had been cooled to 0° C. When addition was complete, the solution was stirred for thirty minutes after which the reaction was quenched by the addition of saturated ammonium chloride solution, followed by 2M hydrochloric acid solution.

The reaction mixture was extracted with diethyl ether and the ether extract was washed successively with water, saturated sodium bicarbonate solution, and then brine. The ether solution was then dried over anhydrous magnesium sulfate, filtered, and evaporated to yield 14 g of 5-hydroxy-3-oxo-6-heptenoic acid, ethyl ester, contaminated with a slight amount of ethyl acetoacetate starting material.

Preparation of β,δ-dihydroxy-6-heptenoic acid, ethyl ester

Employing a syringe, 10 ml of air were bubbled through a solution of 10 mmol of 5-hydroxy-3-oxo-6-heptenoic acid, ethyl ester and 11 mmol of tributylborane dissolved in 10 ml of anhydrous tetrahydrofuran which was under a nitrogen atmosphere. The resulting mixture was stirred overnight, then cooled to −78° C. after which 12 mmol of sodium borohydride were added. The suspension was allowed to warm slowly to 0° C., at which point the reaction was quenched by the addition of 30 mmol of glacial acetic acid. Methanol (30 ml) was added, followed by 3.3 ml of 30% aqueous hydrogen peroxide solution. This mixture was stirred at 0° C. for sixty minutes, and then partitioned between diethyl ether and water.

The organic layer was separated, washed with brine solution, and then dried over anhydrous magnesium sulfate. The ether solution was evaporated to yield crude β,δ-dihydroxy-6-heptenoic acid, ethyl ester which was used in the subsequent step without further purification.

Preparation of 6-ethenyl-2,2-dimethyl-1,3-dioxane-4-acetic acid, ethyl ester

The crude β,δ-dihydroxy-6-heptenoic acid, ethyl ester from the previous step was dissolved in a mixture of 30 ml of dichloromethane and 10 ml of 2,2-dimethoxypropane. Camphorsulfonic acid (0.05 g) was added, and the mixture was stirred overnight. Concentration of the reaction mixture and flash-chromatography of the residue yielded 1.1 g of 6-ethenyl-2,2-dimethyl-1,3-dioxane-4-acetic acid, ethyl ester.

The infrared spectrum of a liquid film of the product showed principal absorption peaks at 2994, 1743, 1439, 1382, 1203, and 1170 cm$^{-1}$ The 90 MHz proton magnetic resonance spectrum of a deuterochloroform solution of the product showed peaks at 1.2–1.5 (m, 10H), 1.60 (m, 1H), 2.48 (m, 2H), 3.75 (m, 1H), 4.05 (1, 2H, J=7 Hz), 4.35 (m, 1H), 5.0–6.0 (m, 3H) parts per million downfield from tetramethyl silane.

We claim:

1. A compound of structural Formula I

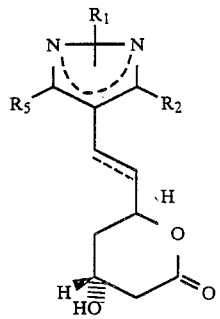

wherein $R_1$ is 2-, 3-, or 4-pyridinyl, and wherein $R_1$ is attached to one of the nitrogen atoms of the pyrazole nucleus;

$R_2$ is alkyl of from one to three carbon atoms or trifluoromethyl;

$R_5$ is

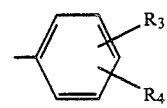

where $R_3$; is alkyl of from one to three carbon atoms, chlorine or fluorine, and $R_4$ is hydrogen, alklyl of from one to three carbon atoms, chlorine, or fluorine; or a ring-opened hydroxy acid derived therefrom or a pharmaceutically acceptable salt thereof.

2. A compound in accordance with claim 1 having the name trans-(±)-6-[2-[5-(4-fluorophenyl)-3-(1-methylethyl)-1-(2-pyridinyl)-1H-pyrazol-4-yl]ethyl]tetrahydro-4-hydroxy-2H-pyran-2-one.

3. A compound as defined in claim 1 having the name trans-(±)-6-[2-[5-(4-fluorophenyl)-3-(1-methylethyl)-1-(2-pyridinyl)-1H-pyrazol-4-yl]ethenyl]tetrahydro-4-hydroxy-2H-pyran-2-one.

4. A pharmaceutical composition, useful as a hypocholesterolemic agent, comprising a hypocholesterolemic effective amount of a compound in accordance with claim 1 in combination with a pharmaceutically acceptable carrier.

5. A method of inhibiting cholesterol biosynthesis in a patient in need of such treatment by administering to said patient an effective amount of a pharmaceutical composition as defined by claim 4.

* * * * *